(12) United States Patent
Poetschke (10) Patent No.: US 11,684,714 B2
(45) Date of Patent: Jun. 27, 2023

(54) AMBULATORY INFUSION DEVICE DRIVE CONTROL AND BLOCKAGE DETECTION

(71) Applicant: Roche Diabetes Care, Inc., Indianapolis, IN (US)

(72) Inventor: Markus Poetschke, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 169 days.

(21) Appl. No.: 16/779,010

(22) Filed: Jan. 31, 2020

(65) Prior Publication Data

US 2020/0164142 A1   May 28, 2020

Related U.S. Application Data (63) Continuation of application No. PCT/EP2018/071135, filed on Aug. 3, 2018.

(30) Foreign Application Priority Data

Aug. 3, 2017   (EP) .................................... 17184773

(51) Int. Cl.
*A61M 5/168*   (2006.01)
*A61M 5/142*   (2006.01)
*H02P 8/34*   (2006.01)

(52) U.S. Cl.
CPC .... *A61M 5/16831* (2013.01); *A61M 5/14248* (2013.01); *H02P 8/34* (2013.01);
(Continued)

(58) Field of Classification Search
CPC .... A61M 2005/16863; A61M 2205/18; A61M 2205/50; A61M 5/14248; A61M 5/16831; H02P 8/34
See application file for complete search history.

(56) References Cited

U.S. PATENT DOCUMENTS

2012/0022494 A1   1/2012   Kirkpatrick
2012/0192951 A1*  8/2012   Yodfat .............. A61M 5/16831
                                                    137/551
(Continued)

FOREIGN PATENT DOCUMENTS

EP   3 172 441 A1   5/2017
JP   2017-038492 A   2/2017
(Continued)

OTHER PUBLICATIONS

Extended European Search Report, EP 17 184 773.4, dated Jan. 26, 2018, 10 pages.
(Continued)

*Primary Examiner* — Quynh-Nhu H. Vu
(74) *Attorney, Agent, or Firm* — Bose McKinney & Evans LLP (57) ABSTRACT

A device and method for controlling operation of an ambulatory infusion device drive. The drive may have a spindle drive with a stepper motor, a drive member operatively coupled to a rotary encoder, and a driver controller that executes several steps, including actuating the stepper motor to execute a requested number of steps in a current drive control sequence, receiving a drive member position that indicates an actual position of a drive member following the actuation, computing an executed steps number from the drive member position, computing a missed steps number for the current drive control sequence, which is the difference between the requested number of steps and the executed steps number, determining when the ambulatory infusion device drive is blocked based on a statistical evaluation of a time-distribution of the missed steps number over a history of drive control sequences, and generating a blockage alarm signal.

13 Claims, 3 Drawing Sheets

(52) U.S. Cl.
 CPC ............ *A61M 2005/16863* (2013.01); *A61M 2205/18* (2013.01); *A61M 2205/50* (2013.01)

(56) References Cited

U.S. PATENT DOCUMENTS

| | | |
|---|---|---|
| 2014/0039396 A1 | 2/2014 | Geipel et al. |
| 2014/0055073 A1* | 2/2014 | Favreau .................. G05B 1/01 |
| | | 318/599 |
| 2014/0278458 A1 | 9/2014 | Borges et al. |
| 2015/0018758 A1 | 1/2015 | John |
| 2016/0266555 A1* | 9/2016 | Favreau ................ A61M 5/172 |

FOREIGN PATENT DOCUMENTS

| | | |
|---|---|---|
| RU | 2013 102 034 A | 7/2014 |
| RU | 2013 150 129 A | 5/2015 |
| WO | WO 2012/140052 A1 | 10/2012 |
| WO | WO 2015/036359 A1 | 3/2015 |

OTHER PUBLICATIONS

International Search Report and Written Opinion of the International Searching Authority, PCT/EP2018/071135, dated Nov. 6, 2018, 11 pages.
Exxelia, AE11—Absolute Optical Encoder, May 2016, 5 pages URL:http://www.exxelia.com./uploads/PDF/ae11-v1.pdf.

* cited by examiner

AMBULATORY INFUSION DEVICE DRIVE CONTROL AND BLOCKAGE DETECTION

RELATED APPLICATIONS

This application is a continuation of PCT/EP2018/071135, filed Aug. 3, 2018, which claims priority to EP 17 184 773.4, filed Aug. 3, 2017, the entire disclosures of both of which are hereby incorporated by reference herein.

BACKGROUND

The present disclosure is in the field of ambulatory infusion devices with a drive. More particularly, it is related to the detection of a blocked drive. The disclosure is further related to determining a drive member position of a drive based on an encoder signal.

Ambulatory infusion devices are well known in the art for example in the therapy of Diabetes Mellitus by Continuous Subcutaneous Insulin Infusion (CSII) as well as in pain therapy or cancer therapy and are available from a number of suppliers. Throughout this document, a design that is particularly suited for CSII is generally assumed for exemplary purposes.

Ambulatory infusion devices that are used for CSII are designed to be carried by a Person with Diabetes (PwD), also referred to as "user," generally continuously night and day. The devices are designed to be carried concealed from view, e.g., with a belt clip or in a trousers' pocket, and/or may be designed to be alternatively carried directly attached to the body via an adhesive pad. Ambulatory infusion devices are designed to infuse liquid drug, in particular insulin, in at least two ways. First, they are designed to infuse liquid drug substantially continuously according to a typically pre-programmed and time variable basal infusion schedule autonomously, i.e., without requiring particular user interactions or operations. Second, they are designed to infuse larger drug boli on demand, for example to compensate for the intake of carbohydrates as well as to correct undesired high blood glucose values. To control these and optional further functions, ambulatory infusion devices comprise an electronics control unit, typically based on one or more microprocessors respectively microcontrollers. "Respectively" is used in this specification, in some cases, to mean "in particular." Throughout this document, the expressions "ambulatory infusion device" and "ambulatory infusion system" refer to a device and system, respectively, with at least the before-described basic functionality. The infusion that is carried out with such devices is in any case a metered infusion of controlled volumes.

According to a classic and well-established design, ambulatory infusion devices or systems are typically of the syringe-driver type where liquid drug is infused out of a liquid drug cartridge by way of controlled and incremental displacement of a cartridge piston. For displacing the cartridge piston, a spindle drive with an electric motor is provided. Typical cartridge volumes are in a range of typically, e.g., 1 ml to 3 ml and store liquid drug, in particular insulin, for a number of days up to a week or more. A number of drawbacks of such devices are known in the art. In particular, they have a limited precision because they involve delivering very small drug amounts, typically in the nanoliter range, out of a drug cartridge having an overall drug volume in the milliliter range.

The drive may use different types of actuators, such as standard DC motors, brushless DC motors or stepper motors. Stepper motors are generally suited because they are comparatively simple to control or actuate and have a defined step-angle that is associated with a well-defined incremental displacement of the cartridge piston and accordingly the metering and infusion of a well-defined incremental drug amount.

Potential occlusions or blockages of the infusion cannula or tubing are a serious issue with ambulatory infusion devices. Such occlusion results in the drive being mechanically blocked. A blocked drive may also occur for other reasons, such as mechanical defect or due to dirt. Throughout this document, the general expressions "blocked" or "blockage" are used for such situations. In practice, however, the expressions "occluded" and "occlusion," as the most common cause for a blocked drive, are used in a largely synonymous way.

Due to a number of reasons, related in particular to the small liquid volumes involved and inherent elasticity, a blocked drive is often hard to detect. Detection, however, is important and should be as early as possible, since a blocked drive results in the drug infusion being interrupted, resulting in severe and potentially fatal medical complications.

For detecting a blocked drive and in particular an occlusion, different approaches have been proposed and implemented for different drive systems, such as motor current measurement for DC motors, the monitoring of the motor axis rotation, and the measurement of an axial reaction force that steeply increases in case of an occlusion.

However, these approaches do not always lead to fully sufficient results and/or require a comparatively complex and costly design, e.g., for realizing a reaction force measurement.

WO 2015/036359 A1 discloses an apparatus for automatic ejection of a fluid. The apparatus has a control unit which is configured to control the apparatus as a function of an actuation step failure number, the actuation step failure number being the number of failed drive train actuation steps since the last successful drive train actuation step.

SUMMARY

This disclosure teaches an improvement to the situation regarding the detection of blockages and occlusions in particular where a stepper motor is used as actuator. In particular, this disclosure teaches how to detect blockages and occlusions within a sufficiently short detection time, while allowing a comparatively simple and cost-efficient design. Further, the risk of false alarms, which are known to be cumbersome and annoying for the user, is favorably small.

According to a first aspect, a drive control unit (also referred to as a "drive controller") for an ambulatory infusion device drive is disclosed. The ambulatory infusion device drive includes a stepper motor, wherein the drive is configured to repeatedly execute a drive control sequence, the drive control sequence comprising the steps of:

a) actuating the stepper motor to a execute a requested steps number in the current drive control sequence;

b) receiving a drive member position, the drive member position being indicative of an actual position of a drive member following the actuation;

c) computing, from the drive member position and the requested steps number, a missed steps number as deviation between the requested steps number and an executed steps number in the current drive control sequence;

d) determining, based on a statistical evaluation of a time-distribution of the missed steps number over a history of drive control sequences, if the drive is blocked.

The drive control unit is further configured, if it is determined that the drive is blocked, to generate a blockage alarm signal.

According to a further aspect, a method for controlling operation of an ambulatory infusion device drive is disclosed. The ambulatory infusion device drive may include a spindle drive with a stepper motor and a rotary encoder in operative coupling with the drive member. The method may further include repeatedly executing a drive control sequence, the drive control sequence comprising:
a) actuating the stepper motor to execute a requested steps number in the current drive control sequence;
b) receiving a drive member position, the drive member position being indicative of an actual position of a drive member following the actuation;
c) computing, from the drive member position and the requested steps number, a missed steps number as deviation between the requested steps number and an executed steps number in the current drive control sequence; and
d) determining, based on a statistical evaluation of a time-distribution of the missed steps number over a history of drive control sequences, if the drive is blocked.

The method may further include generating a blockage alarm signal if it is determined that the drive is blocked.

It is noted that the amount of drug that is infused in step (a) of the drive control sequence is defined by the requested steps number. This requested steps number serves as input value for the method as defined by the generally pre-programmed basal infusion regime in accordance with a doctor's prescription and/or a bolus infusion requested by the user in a specific situation. The amount of drug that is infused and the therapy that is received by the user are accordingly independent from and do not depend on any steps of the method. Consequently, the method does also not affect the doctor's and user's liberty regarding the drug infusion. The method is implemented via design of the drive control unit of an ambulatory infusion device, typically based on corresponding software respectively firmware code.

According to a still further aspect, a computer program product is disclosed that includes a non-transient computer readable medium having stored therein computer program code configured to direct a processor to execute a method according to any embodiment as disclosed before and/or further below. The code may further control a processor to act as drive control unit according to any embodiment as discussed before and/or further below.

According to a still further aspect, an ambulatory infusion device is disclosed that includes a drive and a drive control unit according to either embodiment as disclosed. Further aspects of an ambulatory infusion device in accordance with the present disclosure are discussed further below in the context of exemplary embodiments.

It is to be understood that disclosed methods, devices and computer program products mirror each other and have special corresponding features. Therefore, particular embodiments of a device, in particular a drive control unit, also disclose a corresponding method embodiment or vice versa, even where not explicitly mentioned.

The requested steps number in a drive control sequence is the number of motor steps that shall be executed continuously and in an uninterrupted sequence. The stepper motor may be actuated differently for the different steps. In particular the sequence may have an initial acceleration phase, followed by a steady-state phase, followed by a deceleration phase. The time duration of a single step and accordingly the time per step for which the single stator coils of the stepper motor are powered may in particular be longer in the acceleration and/or deceleration phase as compared to the steady-state phase and may further vary over the acceleration and/or deceleration phase.

Typically, the maximum number of motor steps in a drive control sequence is limited. By way of example, the maximum number of motor steps in a drive control sequence can be 18, with the duration of such sequence being about 20 milliseconds. Other values and in particular more or less steps, however, may be used as well.

In particular for a single incremental basal infusion, a drive control sequence may have only a small number of motor steps, potentially only a single motor step. For larger incremental basal infusions (at a higher basal infusion rate), as well as for the infusion of on-demand boli and for the initial filling (priming) of an infusion line and/or infusion cannula, the control unit is generally configured to control the execution of a number of drive control sequences after each other in accordance with the volume to be infused, with the single drive control sequences being separated by a pause for battery recovery purposes.

The drive member position is an absolute position of the drive member. The drive member is an element of the drive which position can be determined.

The drive member position may be an absolute rotatory position of the drive member. Here and in the following, it is mostly assumed that the drive member is given by the motor axis of the stepper motor and the drive member position is its rotatory position. Alternatively, however, the drive member may also be the rotatory position of another drive element, such as the axis of a reduction gear. Alternatively, the drive member may be a plunger rod as last element (output element of the drive) that is designed to engage a drug reservoir piston and is linearly displaced as the drive is actuated. For such embodiments, the drive member position may be a displacement position relative to a reference position. For the drive member position being a rotatory position, it is measured as angle from an initialization point in time. The initialization point in time may, e.g., be determined by the time where the drug reservoir is replaced and a fresh drug reservoir is initialized for subsequent use. A rotatory drive member position may accordingly have values corresponding to an angle of more than 360°, generally 360° times the number of revolutions of the drive member, e. g, the motor axis. Here, it is generally assumed that the drive member position is given as an angle. It may, however, also be expressed as multiple of the step angle of the stepper motor. The drive member position is determined following the execution of a drive control sequence.

For determining the drive member position, a position sensor is provided as part of or in operative coupling with the drive control unit. For the drive member position being an absolute displacement position respectively linear position as mentioned before, the position sensor may be a linear encoder or other type of linear position sensor as generally known in the art. For the drive member position being a rotatory position, the position sensor may be a rotatory position sensor, in particular a rotatory encoder.

The missed steps number is the difference between the number of steps that the stepper motor is commanded and actuated to execute and the number of steps that is actually executed in a particular drive control sequence. While some missed steps are generally acceptable and known to occur during regular operation even if no occlusion or other fault condition is present, an excessive missed steps number and, in particular, an increase of the missed steps number over time respectively an accumulation of missed steps is indicative of a fluidic occlusion or of the drive being mechanically blocked for other reasons.

Via the statistical evaluation of the time-distribution of the missed steps number over a history of drive control sequences, an increase respectively accumulation of missed steps is determined. The statistical evaluation is favorably designed such that an actual drive blockage respectively occlusion is safely detected at an early point in time, while showing a low risk of false alarms. While the former is a strict requirement in order to prevent medical complications resulting from interrupted drug infusion, the latter is highly desirable from an application point of view. False alarms are known to be very annoying and inconvenient. Further, they often result in the user unnecessarily replacing the infusion line, cannula and/or further disposables, thereby increasing the therapy costs.

In some embodiments, the history of drive control sequences is time-limited. In an exemplary embodiment, the length of the history that is statistically evaluated is limited to the last ten drive control sequences. Other values, however, may be used as well.

In some embodiments, the drive control unit stores score values for pairs of executed steps numbers and a missed steps numbers. The method includes the steps of determining an executed steps number of executed steps in the current drive control sequence, retrieving a score value as determined by the executed steps number and missed steps number, computing a score sum of score values for a pre-determined number of past and preferably consecutive successive sequences, and comparing the score sum with a score sum threshold. It is determined that the drive is blocked if a pre-determined score sum threshold is reached respectively exceeded.

The score values are favorably pre-computed and stored by a memory, typically a non-volatile memory or permanent memory, of the drive control unit. In some embodiments, the score values are stored by way of a lookup table respectively matrix. Ideally, the executed steps number corresponds to the requested steps number. It may, however, also be larger or smaller than the requested steps number, resulting from missed steps, as well as over- or undershoots of the drive member and noise of the drive position determination respectively encoder signal. The score values are favorably determined such that high score values are assigned to a high missed steps number. Alternatively to explicitly storing the individual score values, the score values may be computed from a formula in dependence of the executed steps number and missed steps number.

In some embodiments, the method includes determining if an estimator for a threshold quantile of a distribution of the missed-steps number over a limited history exceeds a pre-determined missed steps threshold. The method may include determining that the drive is blocked if said threshold quantile respectively its estimator reaches respectively exceeds the missed steps threshold. By way of example, the threshold quantile may be the upper $25^{th}$ percentile. As a general rule, the sensitivity of the method for detecting a blockage increases with the threshold quantile increasing and the missed steps threshold decreasing. Further, the sensitivity is dependent on the history length that is considered and increases with decreasing time span. The history length is to be understood as covering a limited number of previous drive control sequences.

In a basic implementation, this type of embodiment may be implemented as follows: A list of the missed steps number is maintained for a pre-determined number of consecutive drive control sequences, with the list being sorted according to the missed steps number. In each drive control sequence, the missed steps number for this drive control sequence is added to the sorted list. At the same time, a value is deleted from the list, such that the number of list entries stays constant, e.g., 7. In each drive control sequence, the deleted value is either of the lowest value (stored as lowest-ranking list element element) or the highest value (stored as highest-ranking list element) of the stored passed missed steps numbers. Deleting of lowest and highest value, however, is not carried out in strictly alternating order, but according to a pre-determined proportion. That is, the lowest value may be deleted in each of a drive control sequences, and deleting the highest value in each of b drive control sequences. Deleting of the lowest value in a drive control sequences and deleting of the highest value in b drive control sequences may be carried out in sequential order, i.e., the lowest value is deleted for a number of a consecutive, drive control sequences, followed by deleting the highest value for a consecutive number of b drive control sequences, and so forth. Alternatively, however, deleting of the lowest value and deleting of the highest value may be carried out according to a different pattern, that results in a desired ratio for deleting the lowest and highest value, respectively. It is found that the value that is stored as middle-ranking element converges to a percentile value that is determined by the relation of a and b after a number of drive control sequences respectively iterations in a satisfying manner. By way of example, the middle-ranking element (for example the element having rank 4 for a list of seven values) converges towards the upper $25^{th}$ percentile for a=1 and b=3.

In some embodiments, the method includes the step of computing, based on the distribution of the missed steps number, a first rate of first order events and a second rate of second order events. A first order event is characterized by the missed steps number of a drive control sequence exceeding a first missed steps threshold. A second order event is characterized by the missed steps number of a drive control sequence exceeding a second missed steps threshold different from the first missed steps threshold. The method further includes computing a weighted sum of first order events and second order events. Determining if the drive is blocked includes comparing the weighted sum with a weighted sum threshold. It may be determined that the drive is blocked if the weighted sum reaches or exceeds the weighted sum threshold. It is noted that this type of embodiment is not limited to a first order and a second order, but may be extended to events of order m=1 . . . M for any desired natural number for M. For the m-th order event, a corresponding m-th rate is computed and a corresponding m-th missed steps threshold is defined. The weighted sum is computed over all M orders.

In a basic implementation, this type of embodiment may be implemented as follows. For each occurrence of a first order event, the time of occurrence is entered to a first shifting register, in particular a First-In-First-Out (FIFO) shifting register. Similarly, for each occurrence of a second order event, the time of occurrence is entered to a separate second shifting register. As time of occurrence, no absolute time is favorably stored, but the value i of a drive control sequence counter, the drive control sequence counter being incremented with each drive control sequence, following an initialization at an initialization point in time, as explained before. Without loss of generality, it is assumed that the first missed steps threshold $MS_1$ is smaller than the second missed steps threshold $MS_2$, for example $MS_1$=3 and $MS_2$=7. With i as the value of the drive control sequence counter at the present point in time, $I_1$ as value of the drive control sequence counter for the oldest first order event as stored in the first shifting register, $I_2$ as value of the drive control sequence counter for the oldest second order event as stored by the second shifting register, and $L_1$, $L_2$ as length of the first and second shifting registers, respectively, the first rate $r_1$ of first order events may be computed as $$r_1 = \frac{L_1 - 1}{i - I_1}.$$

Similarly, the second rate $r_2$ of second order events may be computed as $$r_2 = \frac{L_2 - 1}{i - I_2}.$$

The weighed sum WS may be computed as $$WS = W_1 \times r_1 + W_2 \times r_2,$$

with $W_1$, $W_2$ being pre-determined weighting factors.

In some embodiments, the method includes determining if the current drive control sequence has been correctly executed. The method further includes increasing or decreasing a counter value based the comparison. Determining if the drive is blocked includes comparing the counter value with a counter value threshold. Comparison is to be understood as determination whether the current drive control sequence has been correctly executed.

In some embodiments, the method includes:
d') determining if the missed steps number exceeds a first missed steps threshold, and
d'1) if the missed steps number does not exceed the first missed steps threshold, decrease a score value by a score decrease value,
d'2) or, alternatively, if the missed steps number does exceed the first missed steps threshold, increase the score value by a score increase value.

It may be determined that the drive is blocked if the score value reaches or exceeds a score value threshold. This type of embodiment combines the properties and advantages of before-described embodiments in a particularly efficient implementation.

In some embodiments, the drive control unit is configured, in step (d'1), to set the score value to zero if decreasing the score value by the score decrease value would result in the score value being negative. Step (d'1) is carried out if the first missed steps threshold is not exceeded in the current drive control sequence, indicating that the current drive control sequence has been executed. Setting the score value to zero as indicated above, rather than allowing negative score values, ensures that a long sequence of correctly executed drive control sequences does not result in the build-up of a buffer that would unduly delay or prevent the detection of a later occlusion.

In some embodiments, the score increase value may be either of a first score increase value and a second score increase value. The drive control unit may be configured, in step (d'2), to determine if the missed steps number exceeds a second missed steps threshold, and
d'2a) if the missed steps value exceeds the second missed steps threshold, increase the score value by the second score increase value,
d'2b) or, alternatively, if the missed steps value does not exceed the second missed steps threshold, increase the score value by the first score increase value.

The first missed steps threshold and the second missed steps threshold may be pre-determined, with the second missed steps threshold being different from the first missed steps threshold. The second missed steps threshold may in particular be larger than the first missed steps threshold. The here-described approach with a first missed steps threshold and a second missed steps threshold may be generalized for a larger number of missed steps thresholds in an analogous way using, e.g., a third missed steps threshold, a fourth missed steps threshold and so forth.

In some embodiments, the drive control unit is configured to determine at least one of the missed steps number being below a negative missed steps threshold and/or the missed steps number being below a positive missed steps threshold, and to generate an alarm signal in the affirmative case. Via these steps, a plausibility check for the executed steps number may be implemented. It is determined if the executed steps number is in a reasonable range or whether the executed steps number is prima facie incorrect. The alarm signal may be different from the blockage alarm system and be indicative for a general drive respectively device fault. The steps may be executed for each drive control sequence, e.g., following the computation of the missed steps number.

In some embodiments, the drive control unit is configured to compute an accumulated missed steps number over a number of consecutive drive actuations, and to generate an alarm signal if the accumulated missed steps number exceeds an accumulated missed steps threshold. Via these steps, another plausibility check for the executed steps number is implemented. The steps may be executed for each drive control sequence, e.g., before or after the before described plausibility check.

A position sensor or encoder that is used for determining the drive portion as mentioned before may either be an absolute or an incremental encoder. An absolute encoder provides a signal that directly corresponds to the absolute linear or rotatory position of the drive member. Its sensor may directly be used as drive member position. An incremental encoder, e.g., a magnetic or optical incremental encoder, provides a periodic encoder signal upon the drive member moving. For a rotatory encoder, the period of the periodic encoder signal may be 360°, corresponding to a full rotation, or may be higher, i.e., have more than one cycle per full rotation. For the case of an exemplary ambulatory infusion device as used as CSCII, the drive member position as rotatory poison of the motor axis may cover, e.g., between 500 and 1000 full rotations in typical examples. In any case, for an incremental encoder, the drive member position as absolute position needs to be computed respectively reconstructed from the encoder signal. It is noted that the expression "absolute position" refers to a position in relation to a reference position. Such reference position, however, is not necessarily pre-defined and determined by the mechanical design. Instead, any desired position may in principle serve as reference position. By way of example, the reference position is a position of the drive member when switching the ambulatory infusion device into an active operation mode (frequently also referred to as "RUN" mode), when basal infusion is carried out.

In some embodiments, the drive control unit includes a position determination unit. The position determination unit may be configured to A) receive an encoder signal from an encoder in operative coupling with the drive member, the encoder signal being indicative of a movement of the drive member; and
B) determine, from the encoder signal, the drive member position.

It is noted that the drive member position unit and its embodiments as well as methods for determining a drive position, where not stated differently, are generally independent from other aspects of the present disclosure, in particular the detection of a blocked drive and may be generally used in the context of an ambulatory system control as well as further applications.

In dependence of the encoder design, an encoder raw signal that is provided by the encoder may be of different types and shapes. In some embodiments in particular of an optical encoder, the encoder raw signal may be a pulsed or square signal of high edge steepness. From the encoder raw signal, a binary encoder signal may be generated by way of a Schmitt trigger in hardware or software/computer code. In some embodiments that are also generally assumed in the following, the encoder signal has period of ideally 180°.

In some embodiments of a position determination unit, the encoder signal is a periodic binary signal. The position determination unit may include a shifting register. The position determination unit may be configured to:
B1) receive the encoder signal and enter the encoder signal into the shifting register;
B2) determine a cyclic drive member position from a pre-computed reconstruction lookup table, the reconstruction lookup table comprising pairs of shift register values and associated cyclic drive member positions; and
B3) determine a reconstructed drive member position from the cyclic drive member position and at least one previous reconstructed drive member position.

When actuating the stepper motor to execute a drive control sequence with a number of motor steps as explained before, a position determination is favorably carried out for each motor step. In some embodiments, the position determination may be carried out as a whole for each motor step during the actuation. In view of real-time computation constraints and for the sake of computational efficiency, however, the encoder signal may be continuously fed into a buffer memory, with the position determination being carried out for all motor steps at the end of the drive control sequence.

The expression "cyclic drive member position" refers to a position of the drive member, in particular a rotary position of the drive member, that is obtained from the encoder signal and the reconstruction lookup table. The cyclic drive member position is periodic with the same period as the encoder signal. For the here-assumed exemplary design, the cyclic drive member position is accordingly periodic with a period of 180° and unique identifier for each position within a period.

For this type of embodiment, the encoder signal is entered respectively fed into the shifting register, in particular a FIFO register, as series of "0" values and "1" values. The number of consecutive "0" and "1" values depends, in addition to the encoder design, on the sampling frequency of the binary encoder signal in relation to the rotational speed. For exemplary purposes, it is assumed that the encoder signal is fed into the shifting register as the Least Significant Bit (LSB) and shifting is carried out toward the Most Significant Bit (MSB). The sampling frequency is selected such that more than one "0" value or more than one "1" value generally occurs in sequence. In an exemplary design that is also generally assumed in the following, the encoder signal is periodic with a period of 180° and the sampling is carried out with one sample for each motor step, e.g., 10 samples per period. Ideally, the encoder signal would accordingly, for a continuous actuation of the drive, consist of sequences of 5 consecutive "high" respectively "1" values, followed by 5 consecutive "low" respectively "0" values, and so forth, with each series of consecutive "1" values respectively "0" values corresponding to a rotational angle of 90°.

In practice, however, this is not the case for a number of reasons. First, some "jitter" is typically present when generating the binary signal by way of a Schmitt trigger as explained before and the number of "0" values and "1" values also depends on the (generally not identical) threshold voltages of the raw signal for the rising and falling flange, respectively. Further, the beginning and ending of a drive actuation is connected with uncertainty regarding the rotatory position of the drive member. Further, some amount of missing steps is known and acceptable to occur.

The length of the shifting register is favorably longer than the number of consecutive "0" values and "1" values to be expected, but may be shorter than the total number of samples for a period. In an exemplary implementation, the length of the shifting register is 8, corresponding to 1 byte. The reconstruction lookup table is determined based on the before-mentioned encoder signal, further taking into account the before-mentioned uncertainties and deviations from the ideal behavior.

The reconstruction lookup table may be determined by way of reference measurements where the encoder and an additional reference encoder that provides a reference position signal are synchronously evaluated. Further, different reconstruction lookup tables as explained before may be combined to form the reconstruction lookup table. Further, the reconstruction lookup table may be optimized numerically by minimizing an error, e.g., a sum of squares residuum, between the reconstructed encoder angle and the reference position signal.

As mentioned before, the cyclic drive member position is periodic with a period corresponding to the encoder signal, e.g., 180°, in an exemplary embodiment. The reconstructed drive member position, in contrast, is an absolute position.

For n being an index value for the executed motor steps, indicating the current drive control sequence, the reconstructed drive member position $\theta_n$ as (rotatory) position may be computed in step B3 as $$\theta_n = \theta_{n-1} - 90° + \mathrm{mod}(T - \theta_{n-1} - 90°, 180°) \tag{1}$$

with T as cyclic drive member position and $\theta_{n-1}$ as reconstructed drive member position for the preceding motor step. For the more general case of the cyclic drive member position being periodic with a period per, the following general formula may be applied:

$$\theta_n = \theta_{n-1} - \frac{\mathrm{per}}{2} + \mathrm{mod}\left(T - \theta_{n-1} - \frac{\mathrm{per}}{2}, \mathrm{per}\right) \tag{1a}$$

In some embodiments, the reconstructed drive member position is directly used as the drive member position at the end of each drive control sequence. In further embodiments, the position determination unit is configured to determine, in each drive control sequence, the drive member position from the reconstructed drive member position as explained before and at least one previous reconstructed drive member position by way of a moving average computation.

In an embodiment, the position determination unit is configured to determine if the shifting register value is invalid, to increase, in case of the shifting register value being invalid, an invalid values counter and to generate an alarm signal if the invalid values counter exceeds an invalid values threshold.

Resulting from the encoder signal as explained before, not all possible values of the shifting register (with the expression "value" referring to a bit pattern) are meaningful. Non-meaningful values are referred to as "invalid". By way of example and for the before discussed exemplary design, a pattern "01010101" (with the MSB being leftmost and the LSB being rightmost) is invalid, since it cannot arise from a sequence of "0" values and "1" values as generated by the encoder. While sporadic invalid values may occur, an excessive occurrence is indicative of a device fault or, generally, a hazardous situation.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
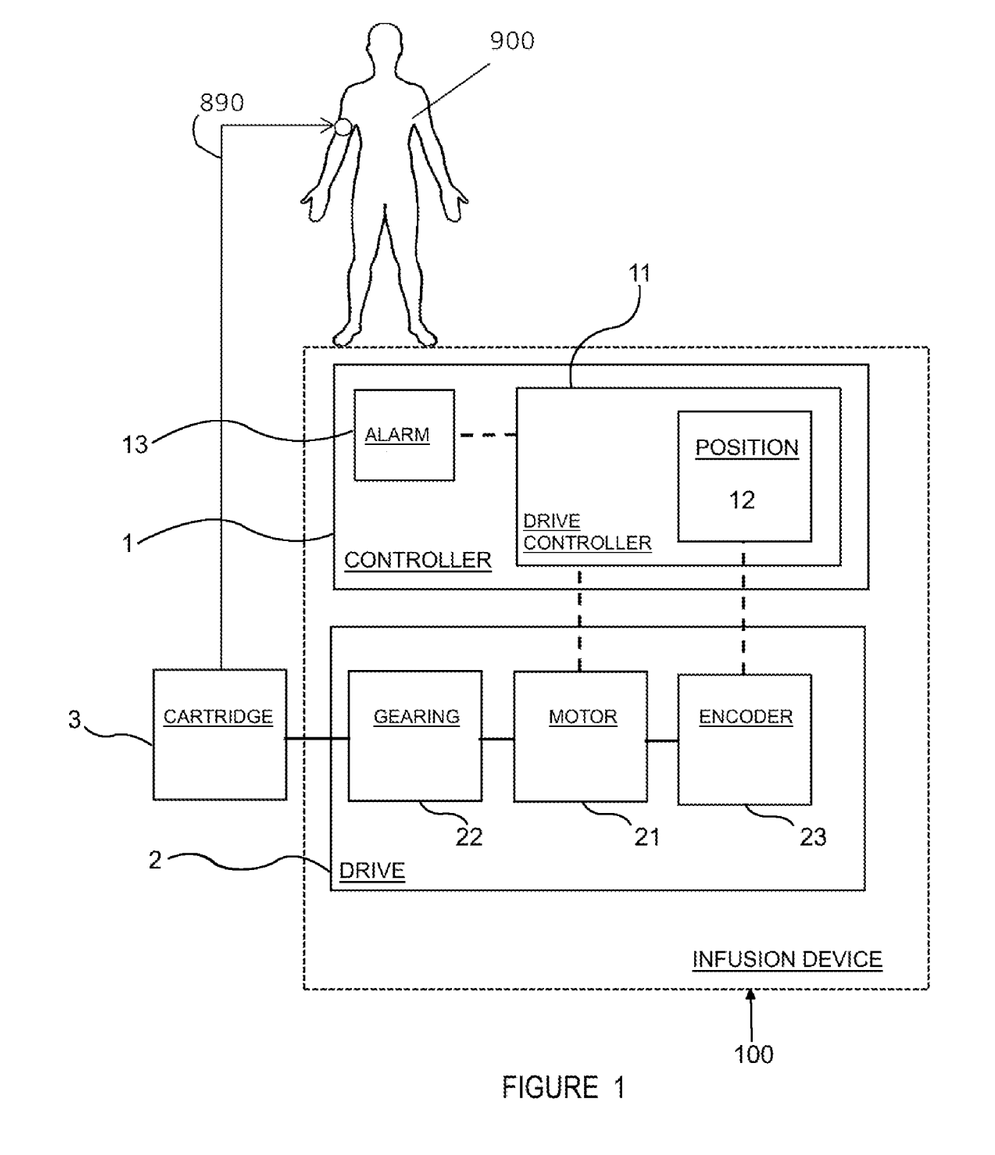
FIG. 1 shows an ambulatory infusion device with an ambulatory infusion device drive unit in a schematic functional view.

In the following, reference is first made to FIG. 1. FIG. 1 shows an ambulatory infusion device 100 in accordance with the present disclosure together with associated elements in a schematic functional view. The ambulatory infusion device 100 includes a control unit 1 (also referred to as a "controller") and a drive 2.

The control unit 1 is generally realized by electronic circuitry and is typically based on one or more processors, such as microcomputers and/or microcontrollers, and may further include peripheral components as well as safety circuitry as generally known in the art.

The one or more processors are configured to execute and operate in accordance with computer program code that is stored as software and/or firmware. The control unit 1 is configured to control overall operation of the ambulatory device 100, in particular for basal drug infusion and/or on-demand bolus infusion as explained above. The control unit 1 includes a drive control unit 11 and the drive control unit 11 (also referred to as "drive controller") includes a position determination unit 12 in accordance with the present disclosure. The control unit 1 further includes an alarming device 13 in operative coupling with the drive control unit 11, the alarming device 13 (also referred to as an "alarm") including one or more of an acoustic or tactile indicator.

The ambulatory infusion device 100 further includes a drive unit 2 that is designed to couple, in an operational configuration, with a drug reservoir 3. The drive unit 2 includes a rotatory stepper motor 21 that is controlled and actuated by the drive control unit 11. The stepper motor 21 acts on a gear unit 22 (also referred to as "gearing"), and the gear unit 22 acts, in an operational configuration, on a cartridge piston that is sealing and sliding received in a cartridge body of a drug cartridge 3, the drug cartridge 3 forming a liquid drug reservoir. The gear unit 22 may include one or more reduction gears. For transforming the rotatory motor that is generated by the stepper motor 21 into a linear displacement of the cartridge piston, a spindle drive unit with a threaded spindle is provided. This overall arrangement of the drive forms a so-called syringe driver.

From the cartridge 3, drug is infused into the body of a user, in particular, patient 900 via an infusion line 890 in a controlled and metered way, in accordance with the displacement of the cartridge piston.

In an embodiment, the ambulatory infusion device 100 is a compact device with a favorably watertight housing, which is designed to further receive the cartridge 3 in a cartridge compartment. In such embodiment, the housing is favorably sized and shaped to be carried, e.g., with a belt clip or in a trousers' pocket. Here, the infusion line 890 typically includes a catheter tubing of, e.g., 0.5 m to 1.5 m length with an infusion cannula. Typically, the ambulatory infusion device is designed for an application time of several years.

In an alternative design, the ambulatory infusion device, in particular the control unit 1 and the drive unit 2, are designed to removably engage a disposable cradle device or cradle, the disposable cradle device being designed to be attached to the user's skin via an adhesive pad. Further, cartridge 3 of such embodiment may be designed to reliably engage the ambulatory infusion device 100 in a side-by-side configuration and to be coupled to the cradle device together with the ambulatory infusion device 100. Upon coupling, the operative coupling between the gear unit 22 and the cartridge piston is established. The threaded spindle of the spindle drive may be an integral part of the cartridge 3 and the drive nut may be part of the gear unit 22, or vice versa, with a releasable coupling between them. For such embodiment, the infusion line 890 may be reduced to an infusion cannula that directly projects from the skin-contacting surface of the cradle device. In such embodiment, the ambulatory infusion device 100 may have an application time of several weeks to several years, while the cradle device and the cartridge 3 may have a typical lifetime in a range of a number of days up to, e.g., two weeks. The ambulatory infusion device 100 is accordingly used with a number of cradle devices and reservoirs in sequence and is accordingly designed to be attached and detached without damage.

In a further design, the ambulatory infusion device 100 and the reservoir 3 are designed as a common device that is favorably sealed in a water-tight manner and designed to be directly adhesively attached to the body. For such design, the whole device is designed for a limited application time of a number of days up to a few weeks and to be subsequently discarded.

A power source, typically in the form of a rechargeable or non-rechargeable battery, may be part of the ambulatory infusion device 100 or be formed as common unit with the cartridge 3. The ambulatory infusion device 100 may further include other components such as a user interface, a display, a data communication unit etc., as generally known in the art. The ambulatory infusion device 100 may further be designed to exchange data with and be remotely controlled by a separate remote control device or diabetes management device. Such device may, among others, be used for programming the basal infusion schedule and requesting the infusion of on-demand drug boli.

Figure 2:
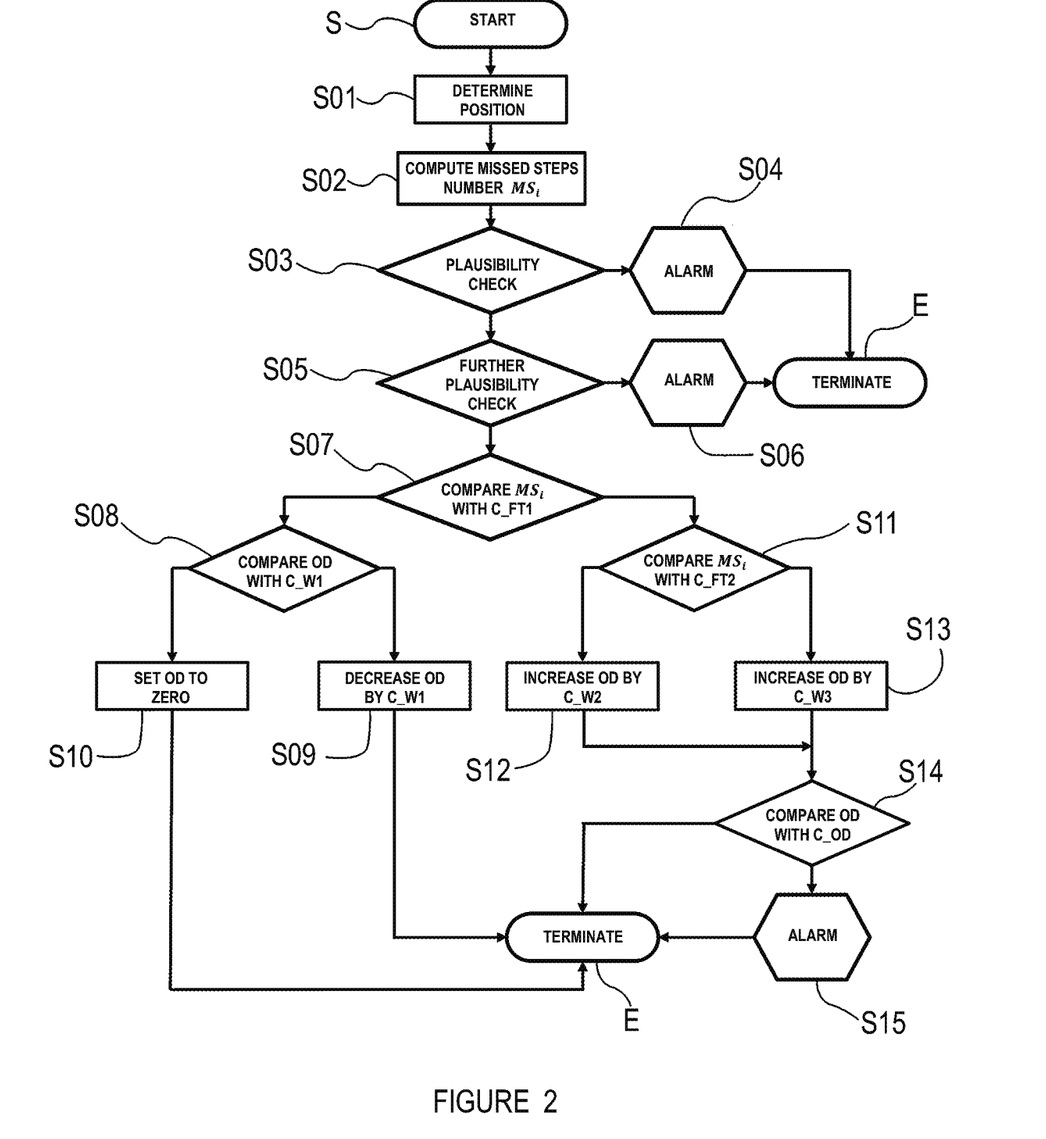
FIG. 2 shows an exemplary operational flow for detecting a blockage or occlusion.

In the following, reference is additionally made to FIG. 2. FIG. 2 shows the operational flow of an exemplary method in accordance with the present disclosure, as executed by the drive control unit 11.

The operations as shown in FIG. 2 are executed as part of each drive control sequence for an incremental basal infusion or as part of an on-demand-bolus infusion. It is noted that in particular an on-demand-bolus infusion is realized by a number of drive control sequences that are executed one after the other, until the total requested bolus amount is infused. It is assumed that the drive 2 has been actuated to execute a requested steps number RS at respectively prior to starting step S and the actuation of the stepper motor 21 is finished for the current drive control sequence. The current drive control sequence is referred to with index i, the directly preceding drive control sequence with i−1, and so forth.

In subsequent step S01, the drive member position is determined by the position determination unit 12. The drive member is the motor axis and the drive member position is its rotational angle φ as absolute rotational angle starting from an initialization as explained above. The value range of the drive member position φ is accordingly m×360°, with m as number of revolutions for emptying the cartridge 3. The position determination unit 12 determines the rotational angle φ as drive member position based on the signal received from the encoder 12 and a reconstruction lookup table as described above in the general description.

In subsequent step S02, the missed steps number $MS_i$ for the current drive control sequence is computed for the current drive control sequence as the difference between the requested steps number RS and the executed steps number. The executed steps number may be computed from the difference of the drive member position for the current and the preceding sequence, $\phi_i - \phi_{i-1}$. In this implementation, the missed steps number is a rotational angle. By dividing it by the step angle of, e.g., 18°, it may be computed as absolute number. Here and in the following, however, it is, as the requested steps number RS, considered as rotational angle.

In subsequent step S03, a plausibility check is carried out in which the missed steps number $MS_i$ for the current drive control sequence is compared against a negative missed steps threshold and a positive missed steps threshold, and the operational flow branches in dependence of the result. The negative missed steps threshold may be a fixed value of, e.g., −72°, and the positive missed steps threshold may be the requested steps number plus a fixed value, e.g., RS+72°. If the missed steps number $MS_i$ is smaller than the negative missed steps threshold or larger than the positive missed steps threshold, the operational flow proceeds with step S04 where an alarm signal is generated and alarming device 13 is activated to provide an error alarm, and the operational flow terminates (step E).

If the missed steps number $MS_i$ is found fine in step S03, the operational flow proceeds with step S05 where a further plausibility check is carried out. An accumulated missed steps number over a history of consecutive drive control sequences is computed. For an exemplary history length of 50, the accumulated missed steps number AMS may accordingly be computed as $AMS = MS_i + MS_{i-1} + \ldots MS_{i-49}$. In step S05, the accumulated missed steps number AMS is compared against an accumulated missed steps threshold, and the operational flow branches in dependence of the result. If the accumulated missed steps number AMS reaches or exceeds the accumulated missed steps threshold, the operational flow proceeds with step S06 where an alarm signal is generated and alarming device 13 is activated, similar to step S04, to provide an error alarm, and the operational flow terminates (step E). The accumulated missed steps threshold may be static, i.e., a fixed and pre-determined value, or may be dynamically adapted. In an exemplary embodiment where the missed steps threshold is dynamically adapted, it may, for example, be computed as 20% of the accumulated requested steps number RS, i.e., as $0.2*(RS_i + RS_{i-1} + \ldots RS_{i-49})$ for an exemplary history length of 50. Other values may be used as well. It is noted that the steps S03/S04 and/or S05/S06 are not essential and may be omitted in a basic embodiment.

If the accumulated missed steps number AMS is found acceptable in step S05, the operational flow proceeds with step S07. In step S07 and the following steps, the core steps of a method for detecting a blocked drive according to the exemplary embodiment are carried out.

In step S07, the missed steps number $MS_i$ is compared with a pre-determined first missed steps threshold C_FT1, and the operational flow branches in dependence of the result. If the missed steps number $MS_i$ does not exceed the first missed steps threshold C_FT1, the operational flow proceeds with step S08.

In step S08, a score value OD is compared with a first occlusion weight C_W1 that corresponds to a score decrease value, and the operational flow branches in dependence in the result. If the score value OD equals or is larger than the first occlusion weight C_W1, the operational flow proceeds with step S09 where the score value OD is decreased by the first occlusion weight C_W1. Otherwise, the score value OD is set to zero in Step S10. Via these steps, the score value OD is generally decreased by the first occlusion weight C_W1, but does not become negative. In both cases, the operational flow subsequently terminates for the current drive control sequence (step E).

If it is determined in step S07 that the missed steps number $MS_i$ exceeds the first missed steps threshold C_FT1, the operational flow proceeds, following step S07, with step S11. In step S11, the missed steps number $MS_i$ is compared with a second missed steps threshold C_FT2 that is higher than the first missed steps threshold C_FT1, and the operational flow again branches in dependence of the result.

If the missed steps number $MS_i$ does not exceed the second missed steps threshold C_FT2, the operational flow proceeds with step S12 where the score value OD is increased by a second occlusion weight C_W2 that corresponds to a first score increase value. If the missed steps number $MS_i$ does exceed the second missed steps threshold C_FT2, the operational flow proceeds with step S13 where the score value OD is increased by a larger third occlusion weight C_W3 that corresponds to a second score increase value and is larger than the second occlusion weight C_W2.

In both cases, the operational flow subsequently proceeds with step S14 where the score value OD is compared with a score value threshold C_OD and the operational flow branches in dependence of the result.

If the score value OD exceeds the score value threshold C_OD, the operational flow proceeds with step S15 where a blockage alarm is generated and the alarming device 13 is activated to provide a blockage or occlusion alarm, and the operational flow terminates (step E). Otherwise, the operational flow directly terminates, following step S14, for the current drive control sequence.

As mentioned before, the procedure according to FIG. 2 is generally executed for each drive control sequence. If, however, an alarm is generated (steps, S04, S06, S15), no further drive control sequences are executed. Instead, the control unit 1 controls the ambulatory infusion device 100 to switch into an error mode where all infusion is stopped.

Figure 3:
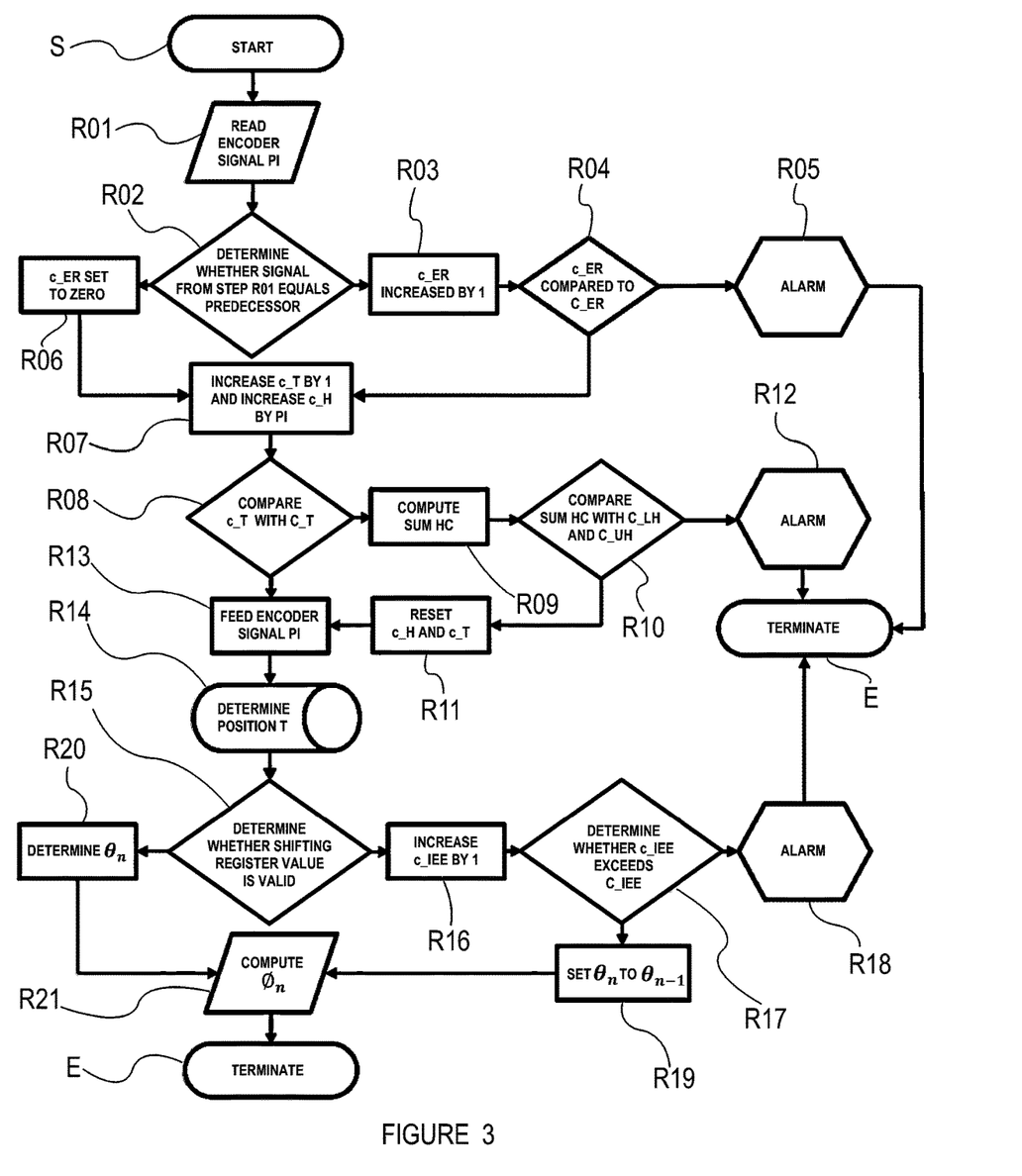
FIG. 3 shows an exemplary operational flow for determining a drive member position.

In the following, reference is additionally made to FIG. 3. FIG. 3 shows the operational flow of an exemplary method for determining the drive member position, in particular, rotational angle φ of the motor axis as explained before. The method is carried out by the position determination unit 12, in particular, the drive control unit 11. The method is carried out following each actuation of the stepper motor 21 to execute a motor step, starting with S.

In step R01, the encoder signal P1 from rotatory encoder 23 is read as binary signal, having either of a "0" value or "1" value. In subsequent step R02, it is determined whether the signal as read in step R01 equals its direct predecessor and the operational flow branches in dependence of the result.

In the affirmative, case, the operational flow proceeds with step R03 where an equal value counter c_ER is incremented by 1. In subsequent step R04, the equal value counter c_ER is compared with a pre-determined equal value counter threshold C_ER and the operational flow branches in dependence of the result. In the affirmative case, the operational flow proceeds with step R05 where an alarm signal is generated and alarming device 13 is activated to provide an error alarm, and the operational flow terminates (step E). Here, number of consecutive "0" values or "1" values is higher than what is possible according to the device design, thereby indicating a device malfunction and/or a yet undetected blockage/occlusion. If the test is negative in step R04, the operational flow proceeds with step R07 as explained further below.

If the test is negative in step R02, i.e., the read signal is different from its predecessor, the operational flow proceeds with step R06 where the equal value counter c_ER is set to zero respectively reset and the operational flow also proceeds with step R07.

In step R07, a counter c_T for the total number of readings of the encoder signal P1 is incremented by one. Further in step R07, a consecutive high counter c_H is incremented by the value of the encoder signal P1, i.e., is incremented by 1 if the encoder signal P1 is a "1" value, and remains unchanged otherwise. The consecutive high counter c_H counts the number of consecutive "1" values of the encoder signal P1 for purposes as explained further below.

Following R07, the operational flow proceeds with step R08 where the counter c_T is compared with a pre-determined encoder readings threshold C_T and the operational flow branches in dependence of the result. If the counter c_T equals the encoder readings threshold C_T, the operational flow proceeds with step R09. In step R09, a sum HC of "1" values over a moving window of past encoder readings is computed, with the window length being determined by the consecutive high counter c_H.

Following step R09, the operational flow proceeds with step R10, where the sum HC as determined in step R09 is compared with a pre-determined lower threshold value C_LH and a pre-determined upper threshold value C_UH. If the sum HC is within the range as defined by the lower threshold value C_LH and an upper threshold value C_UH, the operational flow proceeds with step R11 where the consecutive high counter c_H and the counter c_T are set to zero, i.e., reset.

In combination, steps R08, R09, R10 and R11 implement a statistical test that checks if the high and low counts of the recent past differ significantly from the theoretical ratio. Principally this could be achieved with a moving sum or moving average filter. However, when a large history size (e.g., 1000 data points) is considered, such a straightforward approach requires a substantial amount of memory and is disadvantageous for implementation in the drive control unit. In the implementation of steps R08 to R11 as explained before, the considered history is clustered in several sub groups (e.g., size 100 data points) and the averages/moving sums are calculated for each of these clusters. Subsequently, the moving averages/moving sums over the results for the subgroups is calculated. This approach results in a drastic reduction in the memory consumption, while preserving the original intention.

If the sum HC is not within the range as defined by the lower threshold value C_LH and an upper threshold value C_UH, the operational flow proceeds with step R12 where an alarm signal is generated and alarming device 13 is activated to provide an error alarm, and the operational flow terminates (step E). Steps of R07, R08, R09, R10, R11, R12, in combination, asses the number of "1" readings in groups of a size as determined by the readings threshold $C_T$. An alarm is provided if this value not in a plausible range as defined by the lower threshold value C_LH and an upper threshold value C_UH. A non-plausible value may occur in case of a yet undetected blockage/occlusion, or in case the encoder signal P1 is systematically corrupted. Steps R07-R12 are related to a plausibility check respectively statistical test of whether the distribution of "0" readings and "1" readings of the encoder signal over a time-limited history of motor steps can be assumed to follow an equal distribution which should be ideally the case. It is noted that for a different encoder design and considering the generation of the binary signal via a Schmitt trigger, the distribution of "0" values and "1" values may be systematically non-equal, and the algorithm may be modified accordingly.

It is noted that the steps that are related to the assessment detection of the consecutive number of equal encoder signal P1 readings as well as the distribution of "0" readings and "1" readings" are additional safety measures and may in principle be omitted in a basic embodiment.

In step R13, the binary encoder signal P1 is fed as LSB into a 1-byte shifting register of the position determination unit 12. In subsequent step R14, a cyclic drive member position T is determined from the value of the shifting register and a pre-computed reconstruction lookup table as explained in the general description. An exemplary lookup table that may be used in the present context is provided as Annex I.

In subsequent step R15, it is determined whether the value of the shifting register is valid. If this is not the case, the operational flow proceeds with step R16 where an invalid values counter c_IEE is incremented by 1 and the operational flow proceeds with step R17. In step R17 it is determined whether the invalid values counter c_IEE exceeds an invalid values threshold C_IEE. If this is the case, the operational flow proceeds with step R18 where an alarm signal is generated and alarming device 13 is activated to provide an error alarm, and the operational flow terminates (step E). Otherwise, the operational flow proceeds with step R19 where a reconstructed drive member position $\theta_n$ is set to its predecessor $\theta_{n-1}$ as determined for the preceding motor step.

If the value of the shifting register is determined to be valid in step R15, the operational flow proceeds with step R20 where the reconstructed drive member position $\theta_n$ is determined according to Eqn. 1 of the general description. In subsequent step R21, the drive member position $\phi_n$ for the current motor step is finally computed as moving average over the present a number of, e.g., the last four or five previous reconstructed drive member positions.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

ANNEX I

| Bit pattern (EB) | Cyclic drive member position (T) |
|---|---|
| 00000000 | 164.77 |
| 00000001 | 141.82 |
| 00000010 | 171.90 |
| 00000011 | 157.44 |
| 00000100 | 158.91 |
| 00000101 | 141.95 |
| 00000110 | 160.36 |
| 00000111 | 162.27 |
| 00001000 | 165.40 |
| 00001001 | 152.59 |
| 00001010 | C_IET |
| 00001011 | 146.69 |
| 00001100 | 150.98 |
| 00001101 | 149.45 |
| 00001110 | 143.50 |
| 00001111 | 150.31 |
| 00010000 | 172.92 |
| 00010001 | C_IET |
| 00010010 | 137.12 |
| 00010011 | 137.65 |
| 00010100 | C_IET |
| 00010101 | C_IET |
| 00010110 | C_IET |
| 00010111 | 160.72 |
| 00011000 | 152.06 |
| 00011001 | 153.18 |
| 00011010 | C_IET |
| 00011011 | 165.32 |
| 00011100 | 160.17 |
| 00011101 | 132.90 |
| 00011110 | 134.76 |
| 00011111 | 135.29 |
| 00100000 | 167.11 |
| 00100001 | CIET |
| 00100010 | CIET |
| 00100011 | 117.34 |
| 00100100 | 116.13 |
| 00100101 | C_IET |
| 00100110 | 116.72 |
| 00100111 | 116.89 |
| 00101000 | C_IET |
| 00101001 | C_IET |
| 00101010 | C_IET |
| 00101011 | C_IET |
| 00101100 | C_IET |
| 00101101 | C_IET |
| 00101110 | 166.78 |
| 00101111 | 170.44 |
| 00110000 | 154.73 |
| 00110001 | C_IET |
| 00110010 | 138.26 |
| 00110011 | 113.40 |
| 00110100 | C_IET |
| 00110101 | C_IET |
| 00110110 | C_IET |
| 00110111 | 166.96 |
| 00111000 | 151.39 |
| 00111001 | C_IET |
| 00111010 | 135.35 |
| 00111011 | 124.09 |
| 00111100 | 116.58 |
| 00111101 | 108.07 |
| 00111110 | 114.82 |
| 00111111 | 118.89 |
| 01000000 | 166.76 |
| 01000001 | 170.12 |
| 01000010 | C_IET |
| 01000011 | C_IET |
| 01000100 | C_IET |
| 01000101 | C_IET |
| 01000110 | 98.55 |
| 01000111 | C_IET |
| 01001000 | 97.20 |
| 01001001 | C_IET |
| 01001010 | C_IET |
| 01001011 | C_IET |
| 01001100 | 97.98 |
| 01001101 | C_IET |
| 01001110 | C_IET |
| 01001111 | 98.37 |
| 01010000 | C_IET |
| 01010001 | C_IET |
| 01010010 | C_IET |
| 01010011 | C_IET |
| 01010100 | C_IET |
| 01010101 | C_IET |
| 01010110 | C_IET |
| 01010111 | C_IET |
| 01011000 | C_IET |
| 01011001 | C_IET |
| 01011010 | C_IET |
| 01011011 | C_IET |
| 01011100 | 0.04 |
| 01011101 | 179.27 |
| 01011110 | C_IET |
| 01011111 | 163.02 |
| 01100000 | 151.11 |
| 01100001 | 0.47 |
| 01100010 | C_IET |
| 01100011 | C_IET |
| 01100100 | 110.36 |
| 01100101 | C_IET |
| 01100110 | 97.06 |
| 01100111 | C_IET |
| 01101000 | C_IET |
| 01101001 | C_IET |
| 01101010 | C_IET |
| 01101011 | C_IET |
| 01101100 | C_IET |
| 01101101 | C_IET |
| 01101110 | 172.35 |
| 01101111 | 174.30 |
| 01110000 | 161.44 |
| 01110001 | 179.27 |
| 01110010 | 179.57 |
| 01110011 | 178.64 |
| 01110100 | 106.46 |
| 01110101 | C_IET |
| 01110110 | C_IET |
| 01110111 | 97.97 |
| 01111000 | 97.98 |
| 01111001 | 91.43 |
| 01111010 | C_IET |
| 01111011 | 94.15 |
| 01111100 | 96.61 |
| 01111101 | 106.05 |
| 01111110 | 105.29 |
| 01111111 | 102.10 |
| 10000000 | 16.06 |
| 10000001 | 17.77 |
| 10000010 | C_IET |
| 10000011 | 7.29 |
| 10000100 | C_IET |
| 10000101 | C_IET |
| 10000110 | C_IET |
| 10000111 | 8.47 |

ANNEX I

| Bit pattern (EB) | Cyclic drive member position (T) |
|---|---|
| 10001000 | 85.49 |
| 10001001 | C_IET |
| 10001010 | C_IET |
| 10001011 | C_IET |
| 10001100 | 85.11 |
| 10001101 | C_IET |
| 10001110 | C_IET |
| 10001111 | 9.07 |
| 10010000 | 9.15 |
| 10010001 | 89.23 |
| 10010010 | C_IET |
| 10010011 | C_IET |
| 10010100 | C_IET |
| 10010101 | C_IET |
| 10010110 | C_IET |
| 10010111 | 9.82 |
| 10011000 | 3.92 |
| 10011001 | 90.03 |
| 10011010 | C_IET |
| 10011011 | 8.65 |
| 10011100 | C_IET |
| 10011101 | C_IET |
| 10011110 | C_IET |
| 10011111 | 6.34 |
| 10100000 | 89.41 |
| 10100001 | C_IET |
| 10100010 | C_IET |
| 10100011 | C_IET |
| 10100100 | C_IET |
| 10100101 | C_IET |
| 10100110 | C_IET |
| 10100111 | C_IET |
| 10101000 | C_IET |
| 10101001 | C_IET |
| 10101010 | C_IET |
| 10101011 | C_IET |
| 10101100 | C_IET |
| 10101101 | C_IET |
| 10101110 | C_IET |
| 10101111 | C_IET |
| 10110000 | C_IET |
| 10110001 | C_IET |
| 10110010 | C_IET |
| 10110011 | C_IET |
| 10110100 | C_IET |
| 10110101 | C_IET |
| 10110110 | C_IET |
| 10110111 | C_IET |
| 10111000 | 3.98 |
| 10111001 | 4.91 |
| 10111010 | C_IET |
| 10111011 | 3.91 |
| 10111100 | 25.92 |
| 10111101 | C_IET |
| 10111110 | 89.60 |
| 10111111 | 13.69 |
| 11000000 | 33.77 |
| 11000001 | 25.79 |
| 11000010 | C_IET |
| 11000011 | 26.69 |
| 11000100 | 89.50 |
| 11000101 | C_IET |
| 11000110 | C_IET |
| 11000111 | 26.41 |
| 11001000 | 37.07 |
| 11001001 | C_IET |
| 11001010 | C_IET |
| 11001011 | 30.93 |
| 11001100 | 31.74 |
| 11001101 | 30.67 |
| 11001110 | C_IET |
| 11001111 | 34.53 |
| 11010000 | 71.89 |
| 11010001 | C_IET |
| 11010010 | C_IET |
| 11010011 | C_IET |
| 11010100 | C_IET |
| 11010101 | C_IET |
| 11010110 | C_IET |
| 11010111 | C_IET |
| 11011000 | C_IET |
| 11011001 | C_IET |
| 11011010 | C_IET |
| 11011011 | C_IET |
| 11011100 | 22.73 |
| 11011101 | 8.98 |
| 11011110 | 51.71 |
| 11011111 | 77.64 |
| 11100000 | 43.70 |
| 11100001 | 44.72 |
| 11100010 | 77.66 |
| 11100011 | 29.15 |
| 11100100 | 53.59 |
| 11100101 | 45.22 |
| 11100110 | 49.02 |
| 11100111 | 50.16 |
| 11101000 | 82.34 |
| 11101001 | C_IET |
| 11101010 | C_IET |
| 11101011 | C_IET |
| 11101100 | C_IET |
| 11101101 | C_IET |
| 11101110 | 43.46 |
| 11101111 | 72.19 |
| 11110000 | 61.65 |
| 11110001 | 34.61 |
| 11110010 | 60.29 |
| 11110011 | 57.49 |
| 11110100 | C_IET |
| 11110101 | C_IET |
| 11110110 | C_IET |
| 11110111 | 71.04 |
| 11111000 | 69.11 |
| 11111001 | 70.00 |
| 11111010 | C_IET |
| 11111011 | 87.24 |
| 11111100 | 37.54 |
| 11111101 | 87.93 |
| 11111110 | 44.34 |
| 11111111 | 74.01 |

What is claimed is:

1. A drive controller for an ambulatory infusion device drive having a stepper motor, the drive controller configured to repeatedly execute a drive control sequence, comprising:
   a) actuating a stepper motor to a execute a requested number of steps in a current drive control sequence;
   b) receiving a drive member position that indicates an actual position of a drive member following the actuation;
   c) computing an executed steps number from the drive member position;
   d) computing a missed steps number for the current drive control sequence, which is the difference between the requested number of steps and the executed steps number;
   e) determining when the ambulatory infusion device drive is blocked based on a statistical evaluation of a time-distribution of the missed steps number over a history of drive control sequences, wherein the history is clustered into subgroups and the statistical evaluation considers averages and/or moving sums for each subgroup; and
   f) generating a blockage alarm signal.

2. The drive controller according to claim 1, wherein the history of drive control sequences is time-limited.

3. The drive controller according to claim 1, wherein the drive controller stores score values for pairs of executed steps numbers and missed steps numbers, wherein the drive controller is further configured to:
   retrieve a score value as determined by the executed steps number and missed steps number;
   compute a score sum of score values for a pre-determined number of past consecutive successive drive control sequences; and
   compare the score sum with a score sum threshold.

4. The drive controller according to claim 1, wherein the drive controller is further configured to determine when an estimator for a threshold quantile of a distribution of the missed-steps number over a limited history exceeds a pre-determined missed steps threshold.

5. The drive controller according to claim 1, wherein the drive member position is an absolute rotary position of the drive member.

6. The drive controller according to claim 1, wherein the drive controller is further configured to:
   determine if the current drive control sequence has been correctly executed and increase or decrease a counter value based on the comparison; and
   determine when the ambulatory infusion device drive is blocked at least in part by comparing the counter value with a counter value threshold.

7. The drive controller according to claim 1, wherein the drive controller is further configured to:
   e') determine if the missed steps number exceeds a first missed steps threshold; and
   e'1) when the missed steps number does not exceed the first missed steps threshold, decrease a score value by a score decrease value; and
   e'2) when the missed steps number exceeds the first missed steps threshold, increase the score value by a score increase value;
   wherein determining when the ambulatory infusion device drive is blocked includes determining if the score value exceeds a score value threshold.

8. The drive controller according to claim 7, wherein the score increase value is either of a first score increase value and a second score increase value and the drive controller is configured, in step (e'2) to, when the missed steps number exceeds the first missed steps threshold:
   (i) determine whether the missed steps number exceeds a second missed steps threshold;
   (ii) when the missed steps value exceeds the second missed steps threshold, increase the score value by the second score increase value; and
   (iii) when the missed steps value does not exceed the second missed steps threshold, increase the score value by the first score increase value.

9. The drive controller according to claim 8, wherein the drive controller is further configured to:
   compute a first rate of first order events and a second rate of second order events based on a distribution of the missed steps number, wherein a first order event is characterized by the missed steps number of a drive control sequence exceeding the first missed steps threshold, but not the second missed steps threshold, and a second order event is characterized by the missed steps number of a drive control sequence exceeding the second missed steps threshold; and
   compute a weighted sum of first order events and second order events, wherein determining when the ambulatory infusion device drive is blocked includes comparing the weighted sum with a weighted sum threshold.

10. The drive controller according to claim 1, wherein the drive controller is further configured to:
    compute, based on a distribution of the missed steps number, a first rate of first order events and a second rate of second order events, wherein a first order event is characterized by the missed steps number of a drive control sequence exceeding a first missed steps threshold and a second order event is characterized by the missed steps number of a drive control sequence exceeding a second missed steps threshold different from the first missed steps threshold; and
    compute a weighted sum of first order events and second order events, wherein determining when the ambulatory infusion device drive is blocked includes comparing the weighted sum with a weighted sum threshold.

11. A method for controlling operation of an ambulatory infusion device drive having a spindle drive with a stepper motor, a drive member operatively coupled to a rotary encoder, the method including repeatedly executing a drive control sequence comprising the following steps:
    a) actuating a stepper motor to execute a requested number of steps in a current drive control sequence;
    b) receiving a drive member position that indicates an actual position of a drive member following the actuation;
    c) computing an executed steps number from the drive member position;
    d) computing a missed steps number for the current drive control sequence, which is the difference between the requested number of steps and the executed steps number;
    e) determining when the ambulatory infusion device drive is blocked based on a statistical evaluation of a time-distribution of the missed steps number over a history of drive control sequences, wherein the history is clustered into subgroups and the statistical evaluation considers averages and/or moving sums for each subgroup; and
    f) generating a blockage alarm signal.

12. The drive controller according to claim 1, wherein the controller is configured to consider the history in a cluster of subgroups and the averages and/or moving sums are calculated for each of the clusters.

13. The method according to claim 11, wherein the controller is configured to consider the history in a cluster of subgroups and the averages and/or moving sums are calculated for each of the clusters.

* * * * *